(12) United States Patent
Engvall et al.

(10) Patent No.: US 7,022,090 B1
(45) Date of Patent: Apr. 4, 2006

(54) TRANSPORTABLE APPARATUS FOR TREATING MENIERE'S DISEASE

(75) Inventors: Daniel Engvall, Halmstad (SE); Anders Nilsson, Halmstad (SE)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/763,312

(22) PCT Filed: Aug. 9, 1999

(86) PCT No.: PCT/SE99/01354

§ 371 (c)(1),
(2), (4) Date: Apr. 24, 2001

(87) PCT Pub. No.: WO00/10484

PCT Pub. Date: Mar. 2, 2000

(30) Foreign Application Priority Data

Aug. 19, 1998 (SE) .................................. 9802771

(51) Int. Cl.
*A61H 1/00* (2006.01)

(52) U.S. Cl. ........................................................ 601/76
(58) Field of Classification Search .................. 601/76, 601/77; 607/55–57
See application file for complete search history.

(56) References Cited

U.S. PATENT DOCUMENTS

| 2,652,048 A | 9/1953 | Joers .......................... 128/39 |
| 6,387,076 B1 * | 5/2002 | Landuyt ..................... 604/174 |

* cited by examiner

*Primary Examiner*—LoAn H. Thanh
(74) *Attorney, Agent, or Firm*—Ostrolenk, Faber, Gerb & Soffen, LLP

(57) ABSTRACT

A transportable apparatus for treating Ménière's disease comprises electronically controlled pressure variation unit housed in an inner casing which is partially enclosed by an outer casing provided with an opening covered by a removable cover. A storage compartment is disposed between the casings to receive a flexible tube provided with an ear plug. The flexible tube is connected to the pressure variation unit. The storage compartment surrounds a first portion of the inner casing in which the flexible tube can be disposed in a coiled manner.

10 Claims, 3 Drawing Sheets

TRANSPORTABLE APPARATUS FOR TREATING MENIERE'S DISEASE

FIELD OF THE INVENTION

Figure 1:
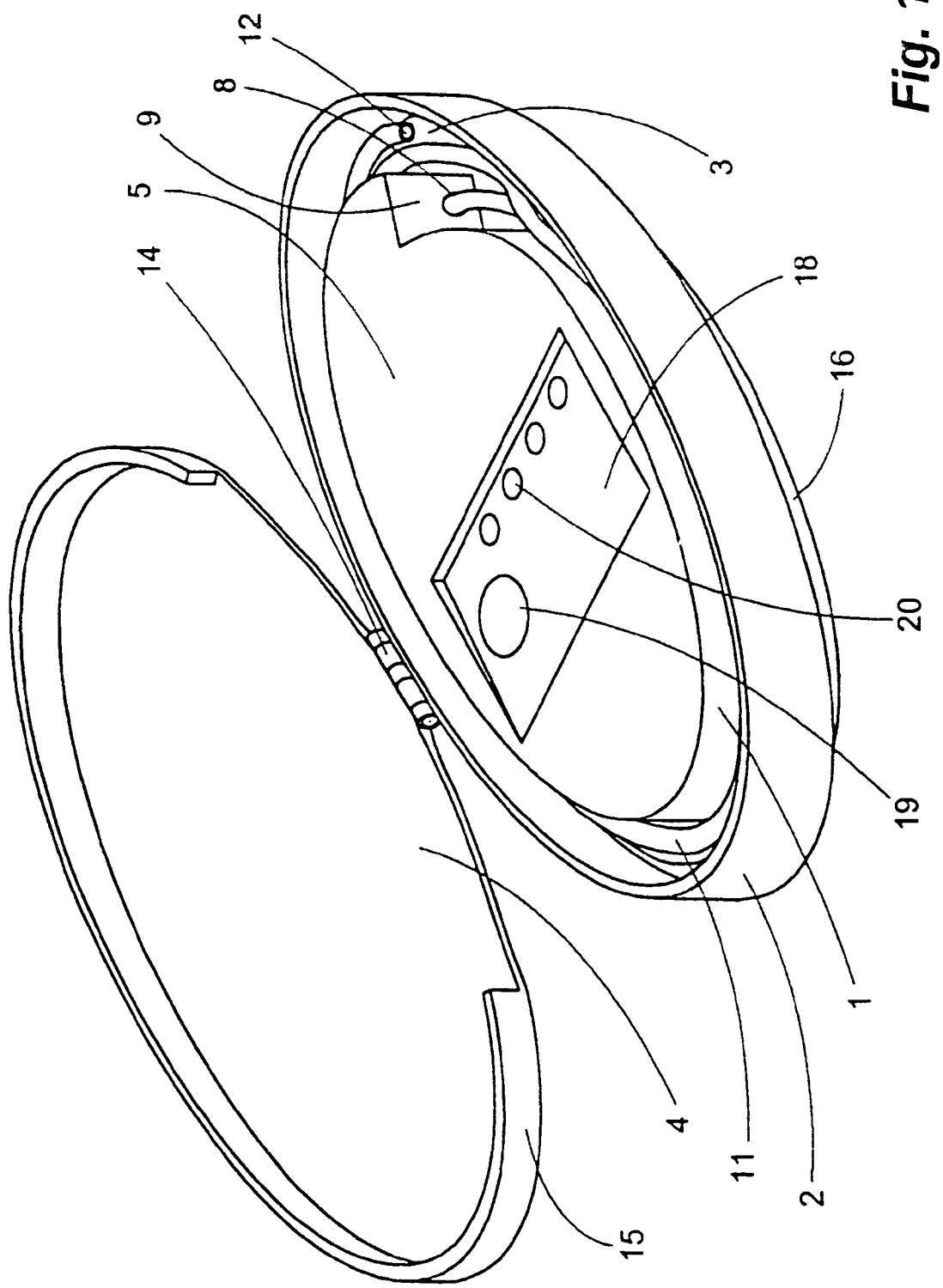

The present invention relates to a transportable apparatus for treating Ménière's disease and similar conditions which affect the pressure balance between the various compartments of the internal ear.

BACKGROUND OF THE INVENTION

Ménière's disease can be treated by affecting the pressure in the internal ear, in particular the endolymphatic system. A number of apparatus for carrying out this treatment are known in the art. They comprise a pressure generating/control unit to which a flexible tube provided with an ear plug is coupled for conducting pressure pulses to a patient's external ear.

WO 83/02556 discloses an apparatus for influencing the hydrodynamic system of the inner of an ear comprising a displaceable diaphragm forming the wall of an air pressure generating chamber, the diaphragm being reciprocally displaceable by means of a crank coupling in a direction away from the chamber against the force of a spring coil.

WO 93/08775 discloses an air pressure generator for the treatment of Ménière's disease by pressure pulses generated by a flexible membrane forming a wall in a pressure generating chamber, the membrane being displaced by actuation means rigidly coupled to the shaft of an electrical motor.

WO 97/23178 discloses a device for affecting the hydrodynamic system of the inner ear comprising first means for generating a static pressure level and second means for causing a variation of that level in accordance with a predetermined program controlled by a control unit. Each of the first and second means comprise a flexible membrane (100, 200). Also in this known apparatus one half of the reciprocating movement of the diaphragm, the one in which the diaphragm moves towards the pressure generating chamber, is caused by spring means.

The design of these apparatus is silent about the patient's need for ambulant treatment. To allow the patient to live a life as normal as possible and, in particular, to travel, it should be possible to administer the treatment wherever the patient happens to be. Since such administration implies that that it would have to be carried out in the absence of competent health care personnel self-administration should be possible. A transportable apparatus for personal use should also be of a design protecting its delicate parts and the flexible tube/earplug from damage and dirt, and its maneuver organs from inadvertent manipulation.

OBJECTS OF THE INVENTION

It is an object of the present invention to provide an apparatus for treatment of Ménière's disease and similar conditions by affecting the pressure in the internal ear which is easy to transport by the patient to be used whenever there is a need for treatment, and which takes into account and solves the aforementioned design problems.

It is another object of the invention to provide such an apparatus which, in addition, can be operated by the patient without assistance by others.

SUMMARY OF THE INVENTION

According to the present invention is provided an apparatus of the aforementioned kind, comprising electronically controlled pressure variation means housed in an inner casing, the inner casing being partially enclosed by an outer casing provided with an opening covered by a removable cover, a storage compartment disposed between the casings, a flexible tube connected to said pressure variation means at its one end and being provided with an ear plug at its other end, the flexible tube being disposable in the storage compartment and removable therefrom with its free end carrying the ear plug for administration of pressure pulses to the external ear of a patient. This solves an important problem since the flexible tube has to be about half a meter long at minimum to allow its ear plug to be fixed to the patient's external ear. If not stored and protected properly it would have a tendency to intertwine and fasten with the ear plug in other gear. This tube length is required for convenient self treatment during which the patient sits at a table while the apparatus rests on the table before him or her.

According to a preferred aspect of the invention the storage compartment surrounds a first portion of the inner casing; preferably the flexible tube is disposed in a coiled manner around that portion. This design provides additional shielding for the most sensitive elements of the apparatus while providing for easy deposition of the tube after a treatment session.

According to a second preferred aspect of the invention the first portion 1a of the inner casing is removable from a second portion 16 of the inner casing. Preferably the second portion 16 of the inner casing and the outer casing are made from one piece of material. By removing the first portion of the inner casing the electronics and the mechanical parts of the apparatus become accessible for adjustment or repair by a technician without having to disassemble the apparatus. Electronic and mechanical elements of a delicate nature can be disposed in a way that makes them face the first portion. Thereby they are optimally protected by being mounted in the innermost part of the apparatus while remaining easily accessible from outside for repair and testing.

Also preferred is to make the flexible tube pass through an opening in the first portion of the inner casing.

According to a third preferred aspect of the invention the first portion of the inner casing is provided with a panel for control of the apparatus by the patient. Thereby an inadvertent start or other manipulation of the apparatus' maneuver organs is prevented.

To protect the patient from damage the apparatus of the invention is confined to working pressures not exceeding 30 cm of water column. This is achieved by providing the apparatus with a pressure sensor and to program the microprocessor to open a safety valve once the maximum tolerable pressure is reached.

Advantageously the apparatus of the invention comprises a rechargeable battery in a battery compartment and an electrical connector for connection to a battery eliminator. The battery compartment is advantageously disposed in a way to make it accessible from the rear (bottom) side of the apparatus, that is, the side on which the apparatus stands when in use.

Figure 2:
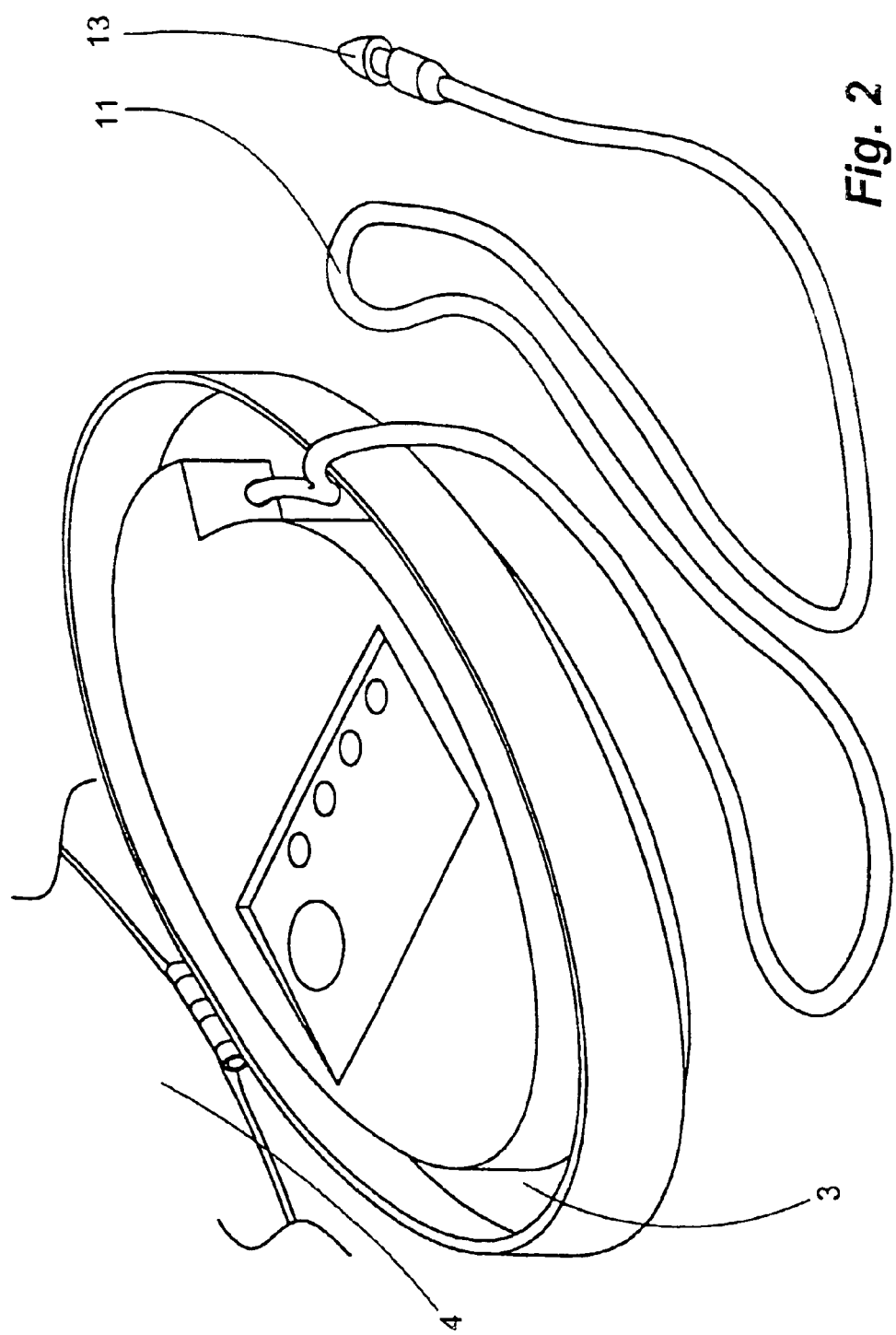
Figure 3:
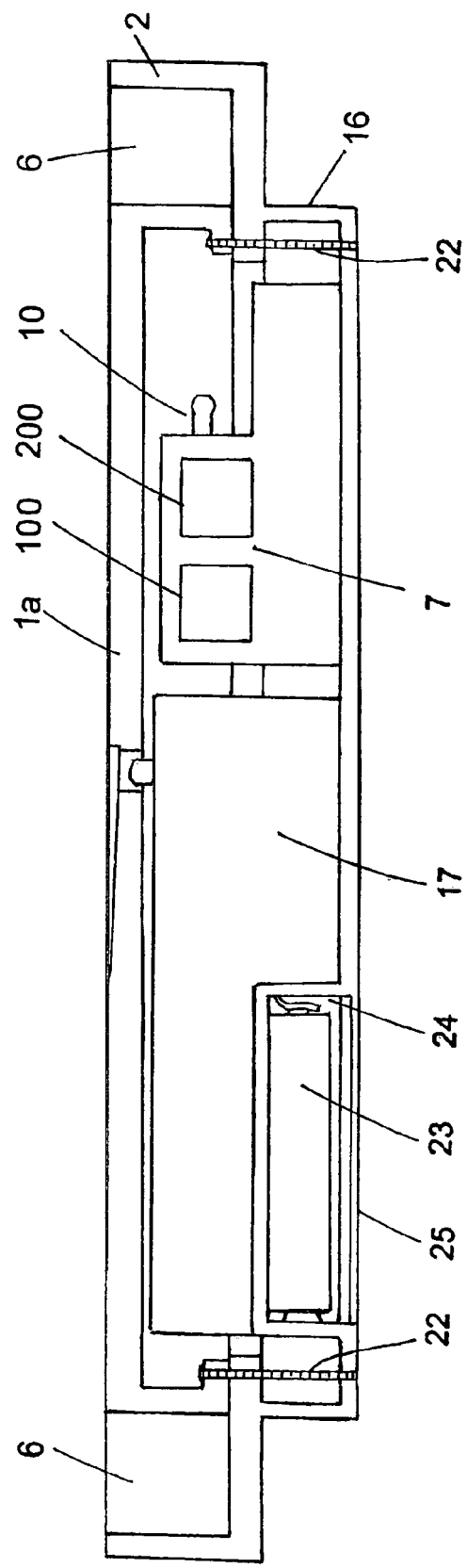

Further preferred features of the present invention are disclosed in the appended claims and a preferred embodiment illustrated in a rough drawing, in which is shown in FIG. 1 the apparatus of the invention, in a side view from above, with the casing cover in an open position, and with the flexible tube in a stored (coiled) condition;

FIG. 2 the apparatus of FIG. 1 and in the same view, with the flexible tube provided with an earplug in an uncoiled position ready for connection to the external ear of a patient;

FIG. 3 the apparatus of FIG. 1, in a vertical section along its largest diameter, without the flexible tube and with the cover in a closed position.

The apparatus of the invention shown in FIGS. 1–3 comprises an inner casing 1 of having about the form of an ellipsoid delimited by two bases perpendicular to its the axis of symmetry and thus parallel to each other. One end portion or the inner casing 1 is surrounded by the wall of an outer casing 2 which is also ellipsoid in form and shares the axis of symmetry casing 1. The ellipsoid wall of the outer casing 2 is spaced apart from the inner casing 1 to which it is joined by a bottom flange 3 forming the peripheral part of what would be its one basis. Thereby an annular space or groove 6 of elliptic form is formed. Any other suitable form of the apparatus, such as a circular form, would be equally possible.

The other (topside) basis of outer casing 2 is lacking. Instead the outer casing 2 is provided with an elliptical flat cover 4 fastened by a hinge 14 to let it be opened and closed. For most of its circumference, except for a portion in the proximity of the hinge 14, the cover 4 is provided with a rim 15 which overlaps a the outer casing 2 wall when the cover 4 is in a closed position in which it can be releaseably secured to the outer casing 2 (not shown). A simple snap lock (not shown) holds the cover 4 in the closed position; it is moulded into appropriate superimposed (when closed) portions of the inside of rim 15 and the outside of the outer casing 2 wail.

The inner casing 1 contains a pressure generating unit 7 for generating the variations in air pressure to be adduced to the external ear of a patient and, from there, to the patient's internal ear through a tiny tube implanted in the tympanic membrane. The pressure generating unit 7 may comprise a diaphragm pump operated by electrically driven actuating means, such as the assembly disclosed in WO 97/23178. It is only indicated in a general way in FIG. 3. The pressurized air outlet of the pressure generating unit 7 has the form of a nipple 10 suitable for attaching one end of a flexible plastic tube 11 the other end of which caries an earplug 13 to be inserted into one of the the patient's external ears.

The flexible tube 11 extends through a circular opening 8 into the elliptical circumferential groove 6 in which it can be wound up when the apparatus of the invention is not being used. This condition is shown in FIG. 1. The free end 12 of the flexible tube 11 normally carries an earplug 13 which has been omitted in FIG. 1 for reasons of clarity. Though being substantially thicker than the flexible tube 11 the earplug 13 can also be stored in the elliptical groove 6 by a design making the groove to widen at a portion 9 of the inner casing 1 wall deviating in the direction of the axis of symmetry of the ellipsoid; the opening 8 is arranged in this wall portion 9.

FIG. 2 shows the apparatus of the invention ready for use. The flexible tube 11 is unwound and disposed for most of its length outside of the apparatus of the invention.

The apparatus in FIGS. 1–3 is intended to be put on a horizontal support with its flat underside, the basis pertaining to the portion of the inner casing 1 extending exteriorly of the outer casing 2.

In addition the inner casing 1 houses an only schematically illustrated electronic control unit 17 including a microprocessor for controlling the generation of the pressure pulses in the pressure generating unit 7. Energy for several treatments can be stored in rechargeable batteries 23 disposed in a separate battery compartment 24 accessible from the underside of the apparatus by removing the compartment lock 25. Miniature contacts accessible from outside for recharging the batteries 23 through a battery eliminator are not shown in the Figures; the same is true for other electrically operated equipment known in the art, such as a valve for equalizing air pressure in the pressure generating unit 7 and a safety valve.

The top wall 5 of the inner casing 1 is provided with a panel 18 for operation of the apparatus by the patient. The panel 18 comprises an on/off touch switch 19 and four diode lights 20 indicating, to the patient: whether the apparatus is pumping or not; the completion of a treatment session; that the manual should be consulted; that there is a leakage.

The portion 1a of the inner casing 1 enclosed by the outer casing 2 is mounted by screws 22 to the combination of the not-enclosed portion 16 of the inner casing and the outer casing 2 which is made in a single piece of a hard polymer material; the same material is used for said mounted portion of the inner casing 1 and the outer casing cover 4. This design provides convenient access to the various parts housed in the inner casing 1.

The apparatus of the invention can be made to a size and a weight which make it convenient to carry. The casings can be manufactured by injection moulding from a variety of polymer materials. A prototype of weighing about 550 g has been tested in patients with good results.

What is claimed is:

1. A transportable apparatus for treating Ménière's disease and similar conditions affecting the pressure balance between the various compartments of the internal ear, comprising a mechanical, electronically controlled pulse generator housed in an inner casing and operable for generating pressure pulses having pulse characteristics adapted for treating Ménière's disease and similar conditions affecting the pressure balance between the various compartments of the internal ear, the inner casing being partially enclosed by an outer casing, a storage compartment disposed between the casings, a flexible tube connected to said mechanical pulse generator at its one end and being provided with an ear plug at its other end, the flexible tube being disposable in the storage compartment and removable therefrom with its free end carrying the ear plug for administration of said pressure pulses to the external ear of a patient, said storage compartment surrounding a first portion of the inner casing around which the flexible tube is disposable in a coiled manner.

2. The apparatus of claim 1, wherein said first portion is removable from a second portion of the inner casing.

3. The apparatus of claim 2, wherein said second portion of the inner casing and the outer casing are made from one piece of material.

4. The apparatus of claim 1, wherein said first portion of the inner casing is provided with a panel for control of the apparatus by the patient.

5. The apparatus of claim 1, wherein the flexible tube passes through an opening in said first portion of the inner casing.

6. The apparatus of claim 1, wherein the pressure pulses do not exceed 30 cm of water column.

7. The apparatus of claim 1, comprising a rechargeable battery in a battery compartment and an electrical connector for connection to a battery eliminator.

8. The apparatus of claim 1, wherein said removable cover is hinged to said outer casing.

9. The apparatus of claim 1, wherein said first portion of said first casing is enclosed within a space defined by said outer casing, while said second portion of said first casing extends beyond said space defined by said outer casing.

10. The apparatus of claim 1, said mechanical pulse generator comprising a first device for generating a static pressure level and a second device for causing a variation of that static pressure level in accordance with a predetermined program.

\* \* \* \* \*